(12) United States Patent
Fischer et al.

(10) Patent No.: US 12,303,661 B2
(45) Date of Patent: May 20, 2025

(54) COUPLING ELEMENT AND COUPLING SYSTEM FOR A CLOSED FLUID TRANSFER SYSTEM

(71) Applicant: B. Braun Melsungen AG, Melsungen (DE)

(72) Inventors: Nathanael Fischer, Hauneck (DE); Florin Kopp, Schortens (DE); Karl Martin Berg, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 217 days.

(21) Appl. No.: 17/908,026

(22) PCT Filed: Mar. 3, 2021

(86) PCT No.: PCT/EP2021/055245
§ 371 (c)(1),
(2) Date: Aug. 30, 2022

(87) PCT Pub. No.: WO2021/175881
PCT Pub. Date: Sep. 10, 2021

(65) Prior Publication Data
US 2023/0086505 A1   Mar. 23, 2023

(30) Foreign Application Priority Data
Mar. 6, 2020   (DE) ............ 10 2020 202 941.1

(51) Int. Cl.
*A61M 39/16*   (2006.01)
*A61M 39/10*   (2006.01)
(Continued)

(52) U.S. Cl.
CPC .......... *A61M 39/165* (2013.01); *A61M 39/26* (2013.01); *A61M 2039/1027* (2013.01);
(Continued)

(58) Field of Classification Search
CPC ......... F16L 37/32; F16L 37/36; F16L 37/367; F16L 29/04; A61M 39/165; A61M 39/26; A61M 2039/1027; A61M 2039/1061
See application file for complete search history.

(56) References Cited

U.S. PATENT DOCUMENTS 2,819,914 A * 1/1958 Eitner .............. F16L 37/367
4,982,736 A * 1/1991 Schneider ........... F16L 37/32
(Continued)

FOREIGN PATENT DOCUMENTS

AU   2013200393 B2   5/2014
AU   2014277764 A1   1/2015
(Continued)

OTHER PUBLICATIONS

DE-202006009462-U1—Machine Translation—English (Year: 2006).*
(Continued)

*Primary Examiner* — William S. Choi
(74) *Attorney, Agent, or Firm* — Christopher A. Rothe; CM Law

(57) ABSTRACT

A coupling member for a closed fluid transfer system includes a housing having a fluid connection and a coupling side. A first channel extends from the fluid connection toward the coupling side for fluidly connecting the fluid connection and the coupling side. An elastomer member surrounds an opening of the first channel, or forms a second channel adjoining the first channel. An elastomer member opening of the second channel is parallel to the longitudinal axis of the housing. The sealing surface is formed between a first position, in which the sealing surface seals the opening or the elastomer member opening of the second channel, and a second position, in which the sealing surface exposes the opening of the first channel or the elastomer
(Continued)

member opening of the second channel for fluid communication with the coupling side.

19 Claims, 3 Drawing Sheets

(51) Int. Cl.
    *A61M 39/26*     (2006.01)
    *F16L 37/367*     (2006.01)

(52) U.S. Cl.
    CPC .............. *A61M 2039/1061* (2013.01); *A61M 2039/262* (2013.01); *F16L 37/367* (2013.01)

(56) References Cited

U.S. PATENT DOCUMENTS

| | | |
|---|---|---|
| 5,061,264 A | 10/1991 | Scarrow |
| 5,201,717 A | 4/1993 | Wyatt et al. |
| 6,077,259 A * | 6/2000 | Caizza |
| 7,004,934 B2 | 2/2006 | Vaillancourt |
| 7,080,672 B2 | 7/2006 | Fournie et al. |
| 7,137,654 B2 | 11/2006 | Segal et al. |
| 7,396,051 B2 | 7/2008 | Baldwin et al. |
| 7,497,848 B2 | 3/2009 | Leinsing et al. |
| 7,628,781 B2 | 12/2009 | Roy et al. |
| 8,196,614 B2 | 6/2012 | Kriheli |
| 8,262,641 B2 | 9/2012 | Vedrine et al. |
| 8,267,127 B2 | 9/2012 | Kriheli |
| 8,287,513 B2 | 10/2012 | Ellstrom et al. |
| 8,870,832 B2 | 10/2014 | Raday et al. |
| 8,915,902 B2 | 12/2014 | Reynolds et al. |
| 8,926,583 B2 | 1/2015 | Ellstrom et al. |
| 9,039,047 B2 | 5/2015 | Imai |
| 9,345,643 B2 | 5/2016 | Okiyama |
| 9,370,466 B2 | 6/2016 | Garfield et al. |
| 9,493,281 B2 | 11/2016 | Ohlin et al. |
| 9,510,997 B2 | 12/2016 | Kriheli et al. |
| 9,541,227 B2 | 1/2017 | Okiyama |
| 9,549,873 B2 | 1/2017 | Barrelle et al. |
| 9,579,258 B2 | 2/2017 | Fukuoka |
| 9,636,278 B2 | 5/2017 | Sanders et al. |
| 9,642,775 B2 | 5/2017 | Sanders et al. |
| 9,724,504 B2 | 8/2017 | Fangrow, Jr. et al. |
| 9,775,979 B2 | 10/2017 | Okiyama |
| 9,820,913 B2 | 11/2017 | Genosar |
| 9,855,192 B2 | 1/2018 | Kim et al. |
| 9,877,895 B2 | 1/2018 | Garfield et al. |
| 9,951,899 B2 | 4/2018 | Py et al. |
| 9,974,939 B2 | 5/2018 | Fangrow, Jr. |
| 9,987,477 B2 | 6/2018 | Winsor |
| 9,993,636 B2 | 6/2018 | Uber, III et al. |
| 9,999,569 B2 | 6/2018 | Kriheli |
| 10,022,301 B2 | 7/2018 | Ivosevic et al. |
| 10,022,531 B2 | 7/2018 | Shemesh |
| 10,058,693 B2 | 8/2018 | Phillips et al. |
| 10,137,237 B2 | 11/2018 | Bengtsson et al. |
| 10,156,306 B2 | 12/2018 | Fangrow |
| 10,206,853 B2 | 2/2019 | Sanders et al. |
| 10,206,854 B2 | 2/2019 | Wu et al. |
| 10,335,536 B2 | 7/2019 | Melander et al. |
| 10,357,430 B2 | 7/2019 | Kriheli et al. |
| 10,376,654 B2 | 8/2019 | Sanders et al. |
| 10,398,627 B2 | 9/2019 | Kriheli |
| 10,441,507 B2 | 10/2019 | Sanders |
| 10,456,329 B2 | 10/2019 | Sanders et al. |
| 10,470,974 B2 | 11/2019 | Sanders et al. |
| 10,518,078 B2 | 12/2019 | Bejhed et al. |
| 10,561,802 B2 | 2/2020 | Kim et al. |
| 10,632,044 B2 | 4/2020 | Garfield et al. |
| 10,682,505 B2 | 6/2020 | Shemesh |
| 10,894,317 B2 | 1/2021 | Garfield et al. |
| 10,945,922 B1 | 3/2021 | Cairns |
| 2003/0032940 A1 | 2/2003 | Doyle |
| 2005/0090805 A1 | 4/2005 | Shaw et al. |
| 2008/0097371 A1 | 4/2008 | Shemesh |
| 2008/0147012 A1 | 6/2008 | Rome |
| 2009/0069783 A1 | 3/2009 | Elstrom et al. |
| 2009/0299295 A1 | 12/2009 | Rubinstein et al. |
| 2011/0282298 A1 | 11/2011 | Agian et al. |
| 2013/0006211 A1 | 1/2013 | Takemoto |
| 2013/0072893 A1 | 3/2013 | Takemoto |
| 2013/0076019 A1 | 3/2013 | Takemoto |
| 2013/0296791 A1 | 11/2013 | Segev et al. |
| 2014/0263322 A1 | 9/2014 | Ghodbane et al. |
| 2015/0123398 A1 | 5/2015 | Sanders et al. |
| 2015/0126958 A1 | 5/2015 | Sanders et al. |
| 2015/0126974 A1 | 5/2015 | Sanders et al. |
| 2015/0258324 A1 | 9/2015 | Chida et al. |
| 2016/0008544 A1 | 1/2016 | Molson et al. |
| 2016/0053923 A1 * | 2/2016 | Leggett |
| 2017/0209682 A1 | 7/2017 | Shemesh |
| 2017/0356580 A1 * | 12/2017 | Huang |
| 2018/0000690 A1 | 1/2018 | Eichelkraut et al. |
| 2018/0028402 A1 | 2/2018 | Kriheli et al. |
| 2018/0161245 A1 | 6/2018 | Kriheli |
| 2018/0200147 A1 | 7/2018 | Sanders |
| 2018/0200148 A1 | 7/2018 | Sanders |
| 2018/0200498 A1 | 7/2018 | Sanders |
| 2019/0000718 A1 | 1/2019 | Kriheli et al. |
| 2019/0046410 A1 | 2/2019 | Shemesh |
| 2019/0053980 A1 | 2/2019 | West et al. |
| 2019/0060171 A1 | 2/2019 | Lee |
| 2019/0290543 A1 | 9/2019 | Mckinnon et al. |
| 2019/0321261 A1 | 10/2019 | Oshinski et al. |
| 2021/0199223 A1 * | 7/2021 | Langer .................... F16L 37/32 |

FOREIGN PATENT DOCUMENTS

| | | |
|---|---|---|
| DE | 202006009462 U1 * | 9/2006 |
| DE | 102019116970 A1 | 12/2020 |
| EP | 2589368 A1 | 5/2013 |
| EP | 3067037 A1 | 9/2016 |
| EP | 3607993 A1 | 2/2020 |
| IL | 214990 A | 6/2013 |
| IL | 257415 B | 1/2020 |
| IL | 257417 B | 11/2020 |
| WO | 2008129550 A2 | 10/2008 |
| WO | 2009035383 A1 | 3/2009 |
| WO | 2011125023 A1 | 10/2011 |
| WO | 2011150037 A1 | 12/2011 |
| WO | 2012117648 A1 | 9/2012 |
| WO | 2014122643 A1 | 8/2014 |
| WO | 2014181320 A1 | 11/2014 |
| WO | 2015017858 A1 | 2/2015 |
| WO | 2015069643 A1 | 5/2015 |
| WO | 2016042544 A1 | 3/2016 |
| WO | 2016199133 A1 | 12/2016 |
| WO | 2017066406 A1 | 4/2017 |
| WO | 2017109776 A1 | 6/2017 |
| WO | 2017183031 A1 | 10/2017 |
| WO | WO-2018087149 A1 * | 5/2018 ............ A61M 39/26 |
| WO | 2019033004 A1 | 2/2019 |
| WO | 2019086589 A1 | 5/2019 |
| WO | 2019135219 A2 | 7/2019 |
| WO | 2019167035 A1 | 9/2019 |
| WO | 2020031174 A1 | 2/2020 |
| WO | 2021019532 A1 | 2/2021 |

OTHER PUBLICATIONS

Search Report received in German Application No. 10 2020 202 941.5 dated Nov. 25, 2020, with translation, 12 pages.
Search Report received in International Application No. PCT/EP2021/055245 dated Jun. 11, 2021, with translation, 5 pages.
Written Opinion received in International Application No. PCT/EP2021/055245 dated Jun. 11, 2021, with translation, 20 pages.

* cited by examiner

COUPLING ELEMENT AND COUPLING SYSTEM FOR A CLOSED FLUID TRANSFER SYSTEM

CROSS-REFERENCE TO RELATED APPLICATIONS

This application is the United States national stage entry of International Application No. PCT/EP2021/055245, filed Mar. 3, 2021, and claims priority to German Application No. 10 2020 202 941.5, filed Mar. 6, 2020. The contents of International Application No. PCT/EP2021/055245 and German Application No. 10 2020 202 941.5 are incorporated by reference herein in their entireties.

FIELD

The invention relates to a coupling member and a coupling system for a closed fluid transfer system.

BACKGROUND

Many substances that are administered as injections or in a comparable form of delivery, such as CMR drugs, which are used in cancer therapy, for example, and whose therapeutic application is primarily aimed at damaging growth-intensive tumor cells, have a considerable hazard potential outside the actual therapeutic application. Due to their mechanism of action, some of these substances are themselves carcinogenic, which is why contact with persons not undergoing therapy must be avoided. Closed drug transfer systems, so called "closed system transfer devices" or CSTDs, are therefore increasingly being used for CMR drugs in the manufacture of ready-to-use preparations. An important component of such CSTDs are coupling systems that enable the safe transfer of CMR drugs or other substances and dry seal after disconnection, thus protecting the environment from contamination, e.g. through leakage or droplet formation on the surfaces of the coupling members. Coupling systems of this type are, in general, associated with the terms "dry connection", "automatic self-sealing technology" or "closed connection" and are essential for the realization of closed fluid transfer systems.

Known coupling systems comprise a female and a male coupling side, which are connectable with each other. This means that different coupling members have to be provided for one purpose. In addition, this design requires the use of adapters for certain procedures, which, for example, enable two syringes to be coupled together.

In addition to the need to keep different coupling members on hand, however, the known coupling systems with different coupling sides also comprise the disadvantage that at least one of the coupling sides provides poor accessibility to the coupling surface that is connected to the other coupling surface during connection. Since the coupling surfaces must be disinfected before use, poor accessibility makes good disinfectability difficult.

Further, some coupling systems have poor flow and/or their coupling surfaces are located in the fluid channel when connected, resulting in fluid residue on the coupling surfaces after disconnection. Similarly, some coupling systems comprise a high priming and residual volume, leading to inefficiency due to non-low residuals in the coupling system. In terms of residual volume, this particularly affects coupling systems with a spring in the fluid channel, which additionally complicates flushing after drug transfer.

SUMMARY

In view of the disadvantages associated with the prior art, it is an object of the present invention to provide a coupling member and a coupling system for a closed fluid transfer system, which are capable of closing dry when the coupling members are disconnected and reducing the number of variants of the coupling members.

According to the invention, the coupling member comprises a coupling member housing comprising a fluid connection and a coupling side, wherein a longitudinal axis of the coupling member housing extends from the fluid connection to the coupling side, a first fluid channel extending from the fluid connection toward the coupling side for fluidly connecting the fluid connection and the coupling side, at least one elastomer member, which surrounds a fluid channel opening of the first fluid channel facing the coupling side and formed in parallel to the longitudinal axis of the coupling member housing, or which forms a second fluid channel adjoining the first fluid channel, wherein an elastomer member opening of the second fluid channel facing the coupling side is formed in parallel with the longitudinal axis of the coupling member housing, and a sealing member having a sealing surface facing the fluid channel opening of the first fluid channel facing the coupling side or the elastomer member opening of the second fluid channel facing the coupling side, wherein the sealing surface is movable along the longitudinal axis of the coupling member housing between a first position, in which the sealing surface seals the fluid channel opening of the first fluid channel or the elastomer member opening of the second fluid channel, and a second position, in which the sealing surface exposes the fluid channel opening of the first fluid channel or the elastomer member opening of the second fluid channel for fluid communication with the coupling side.

Accordingly, a fluid communication of the fluid connection and the coupling side may be formed directly via the first fluid channel or indirectly via the first fluid channel, to which the second fluid channel, which may be formed by the elastomer member, is connected on the coupling side. In the case of a direct fluid connection, the first fluid channel is formed in such a way that the fluid channel opening facing the coupling side is formed parallel to the longitudinal axis of the coupling member housing. For this purpose, the first fluid channel may, for example, run obliquely through the coupling member housing or initially run parallel to the longitudinal axis of the coupling member housing from the fluid connection and bend at an angle to the parallel course on the coupling side. The elastomer member thereby surrounds at least the fluid channel opening of the first fluid channel extending parallel to the longitudinal axis of the coupling member housing.

In the case of indirect fluid communication, the second fluid channel formed by the elastomer member may continue at least a portion of the bent first fluid channel toward the coupling side. Alternatively, in the case of an indirect communication, the first fluid channel may, for example, be formed only parallel to the longitudinal axis of the coupling member housing, wherein the second fluid channel is formed such that it extends at least in sections at an angle to the longitudinal axis for an elastomer member opening formed parallel to the longitudinal axis on the coupling side.

The indirect fluid communication via the elastomer member may have the advantage that different opening cross sections and/or opening positions can be provided, for example, by replacing the elastomer member.

By using the elastomer member for direct or indirect fluid communication, effective sealing may be achieved in the areas or relative positions with respect to the sealing surface or also another elastomer member of a corresponding coupling member to be connected, in which the sealing surface of the sealing member facing the elastomer member or also the surface of the other elastomer member facing the elastomer member are brought into overlap with the elastomer member.

According to the above explanations, the fluid channel opening facing the coupling side for direct fluid communication or the elastomer member opening facing the coupling side for indirect fluid communication of the first fluid channel is not open to the front surface of the coupling side, but to a lateral portion of the coupling side extending from the front surface of the coupling side toward the fluid connection.

In a disconnected state of the coupling member, the sealing surface of the sealing member is in the first position, in which it seals the fluid channel opening facing the coupling side for direct fluid communication or the elastomer member opening facing the coupling side for indirect fluid communication of the first fluid channel. In particular, the sealing surface is formed of an elastic material for sealing to effectively seal the fluid channel opening or elastomer channel opening facing it. Moreover, the sealing surface may be formed by the sealing member only in an area substantially covering the fluid channel opening or elastomer member opening only in one position. In this context, the term "substantially" refers to an arrangement that is adapted in terms of location or dimensions relative to the respective opening, wherein, for example, the sealing surface may be configured to be correspondingly larger due to tolerances, safety requirements and/or manufacturing aspects. Alternatively, however, a larger portion of the sealing member or the entire sealing member may comprise the properties of a sealing surface. For example, the sealing member may thus also provide further seals to the coupling member housing and/or be rotated about an axis parallel to the longitudinal axis of the coupling member housing in order to be able to provide a new sealing surface due to wear.

The configuration of the coupling member according to the invention advantageously enables the use of coupling members of equivalent construction for a closed fluid transfer system.

In an embodiment, the elastomer member is formed from at least two separate elastomers.

The configuration of at least two separate elastomers increases the flexibility of the design of a second fluid channel or also the adaptation of different first fluid channels. The flexibility here refers not only to an arrangement in a plane parallel to the longitudinal axis of the coupling member housing, but may also include an arrangement in a plane perpendicular thereto. In addition, different material pairings may also be applied herein.

In particular, the sealing member can be retained in the first position in the direction of the coupling member housing via a spring member which, on its side facing away from the coupling side, is supported on a fluid connection side portion or on a portion of the coupling member housing located between the fluid connection side portion and the sealing member.

Accordingly, the sealing member may not be moved to the second position, in which the sealing surface exposes the fluid channel opening or the elastomer member opening, without application of external force against the spring force. To increase the force required to move the sealing member from the first position to the second position against the spring force, for example, to reduce the likelihood of unintended movement, the spring may be preloaded.

The spring member may utilize a fluid connection side rear wall as a fluid connection side portion of the coupling member housing for support. Support on a portion of the coupling member housing located between the fluid connection side portion and the sealing member may be used, for example, to reduce the length of the spring member or, more generally, the installation space required for a spring member.

In an embodiment, the spring member is a metal spring or elastomer spring.

Corresponding spring members are available in principle and in a wide variety of designs, so that cost-effective use is possible with different design options.

Alternatively or in addition, the sealing member is elastic at least in sections and is supported on its side facing away from the coupling side on a portion of the coupling member housing on the fluid connection side or on a portion located between the fluid connection side portion and the sealing surface.

For this purpose, the sealing member may be formed at least in sections from an elastic material. Alternatively or in addition, however, the sealing member may also comprise an elastic structure, such as a structure with spring joints, at least in sections.

Accordingly, an additional spring member is not absolutely necessary. However, an additional spring member may be used to provide different counterforces and thus also restoring forces over the range of motion of the sealing member.

In an embodiment, the sealing member is guided between an inner wall of the coupling member housing surrounding the first fluid channel in the longitudinal direction or extending longitudinally on one side of the first fluid channel with respect to the longitudinal axis and an outer wall parallel to the inner wall and spaced apart in the outward direction.

The outer wall parallel to the inner wall may be an external wall of the coupling member housing. Alternatively, the outer wall parallel to the inner wall may be disposed between the inner wall and an external wall of the coupling member housing. The guidance of the sealing member may allow a positionally stable movement of the sealing member, so that in particular the position of the sealing surface of the sealing member relative to the fluid channel opening or elastomer member opening in the first position is not changed by previous movement of the sealing member between the first and second positions. In addition, the guidance may be configured such that the space between the sealing member and a fluid connection side housing portion is sealed by the sealing member. This may prevent the ingress of a fluid.

In particular, the coupling member housing comprises a radial projection on the coupling side with respect to the longitudinal axis and forms a coupling side stop for the sealing member in the first position.

The sealing member in the coupling member housing may be secured against falling out via the interaction of the coupling side stop with the sealing member. In addition, the stop in conjunction with the spring member described above and/or with the at least partially elastic formation of the sealing member may provide a preloading of the spring member and/or the sealing member.

Alternatively or in addition, the sealing member may also be connected to the spring member and/or a housing portion and thus be secured against falling out. However, when connecting the sealing member to a housing portion, care must be taken to ensure that such a connection still permits movement of the sealing surface of the sealing member between the first and second positions.

In a further embodiment, the radial projection is formed by a coupling side portion of the outer wall as described above extending radially inwardly.

If the sealing member is guided between an inner wall of the coupling member housing surrounding the first fluid channel in the longitudinal direction or extending longitudinally on one side of the first fluid channel with respect to the longitudinal axis, and an outer wall spaced in the outward direction parallel to the inner wall, the stop may be implemented in a simple manner in terms of manufacturing technology by the radial projection formed by the coupling side portion. Furthermore, the stop area thus formed is located outside the area of the sealing surface provided for sealing the fluid channel opening or the elastomer member opening.

In a further embodiment, the coupling member comprises, on a coupling side front surface, a closed coupling surface and a coupling side opening limited to an area closable by a side of the sealing member facing the coupling side front surface.

The closed coupling surface is formed on the coupling side front surface by the coupling member housing and the surface of the elastomer member facing the coupling side front surface. Alternatively, the closed coupling surface may also be formed only by the coupling member housing if the latter covers the surface of the elastomer member facing the coupling side front surface. In particular, the closed coupling surface together with the sealing member in the first position forms a substantially flat coupling side front surface of the coupling member. This allows the coupling side to be easily disinfected. In this context, the term "substantially" refers to the fact that individual contour sections may deviate from a planar formation of the front surface, but these do not form any interfering contour that impedes disinfection. For this purpose, the surface of the sealing member facing the coupling side front surface is in particular flush with the closed coupling surface.

In a further development, a rigid surface of the coupling side opening perpendicular to the longitudinal axis is larger than a rigid surface of the closed coupling surface perpendicular to the longitudinal axis, in particular marginally larger. A resulting gap dimension when mating the rigid surface of the coupling side opening and the rigid surface of the closed coupling surface of two coupling members of equivalent design may, for example, be between 0.1 and 0.2 mm.

This allows the use of coupling members of equivalent design for a coupling system comprising these coupling members. The term "equivalent design" includes both identical coupling members and coupling members which are identical only at least in their coupling features for a fluid connection of the coupling members.

When advantageously equivalent coupling members are used, the respective coupling side front surfaces are arranged opposing each other in a mirror-inverted manner, i.e. rotated by 180° to each other about the longitudinal axis. The sealing surfaces of the respective coupling members facing the coupling side front surface are opposite the closed coupling surfaces of the other coupling member. If the coupling members are now moved towards each other, the closed coupling surface of the respective coupling member may engage in the coupling side opening of the respective other coupling member and thus move the respective sealing members into the second position when the coupling members are moved further towards each other. Accordingly, the term "surface" is also not directed to an absolute area dimension, but may be defined by the outer contour of the surface or by another area of the surface, such that the described engagement is made possible. The term "rigid surface" is directed to the fact that the respective surfaces may also comprise elastic portions, as will be described later with respect to a radially outwardly directed housing projection. These elastic portions are considered for the rigid surface only to the extent that they are to be considered at maximum compression.

In particular, the rigid surface of the coupling side opening perpendicular to the longitudinal axis is only marginally larger than the rigid surface of the closed coupling surface perpendicular to the longitudinal axis. The term "marginally larger" refers to the fact that the projecting engagement of the closed coupling surface in the coupling side opening is made possible, but preferably the elastomer members of the coupling members, which are guided over one another in the process, seal against one another on their mutually facing surfaces parallel to the longitudinal axis. In other words, the rigid surface of the coupling side opening is larger at least in the area of the elastomer members only by an amount that may be compensated for by the expansion properties of the elastomer members.

In an embodiment, an external wall of the coupling member housing extending in the direction of the longitudinal axis, in particular a region of the external wall located on a side of the first fluid channel facing away from the sealing member, comprises a housing projection projecting radially outwardly with respect to the longitudinal axis.

Via the housing projection, the coupling member may be retained in a connected state with another coupling member. In such a connected state, the sealing member is in the second position such that the fluid channel opening or elastomer member opening is exposed for fluid communication by the sealing member. Alternatively or in addition, however, the housing projection may cooperate with a stop of the other coupling member to be connected and thus act as a movement limiter. This may prevent the coupling member from being moved beyond a position in which a connected state is reached, so that a fluid communication is prevented or a fluid escapes into areas that are not intended for this purpose.

In particular, the housing projection may be in the form of an elastic snap hook.

The elastic snap hook allows for easy implementation of a releasable connection in a connected state. To release the connection, the snap hook may be moved against its projection direction via an actuation of an unlocking mechanism. Alternatively or in addition, the snap hook may be formed in its engagement region from an elastic material that is temporarily compressed by the engagement region by a tensile force applied for release. Such compression may also be present upon insertion of the snap hook, wherein the snap hook expands elastically again upon reaching the engagement region.

Insofar as the snap hook forms part of the coupling side front surface, it is to be attributed to the closed coupling surface. If the engagement region of the snap hook itself is not elastic, but is formed elastically via flexible holders, the snap hook is spaced from the rest of the closed coupling surface by the clearance for movement to be provided perpendicular to the longitudinal axis. Despite the gap thus formed, this configuration is included in the closed coupling surface.

In a further development, the coupling member housing comprises an undercut on an inner surface of the coupling member housing, in particular the inner surface of the protruding outer wall, in particular an undercut formed by the radial projection forming a coupling side stop for the sealing member in the first position.

The undercut serves to receive a radially outwardly projecting projection of another coupling member to be connected. When coupling members of equivalent design are used, the undercut thus serves to receive the radially outwardly projecting housing projection, in particular the snap hook. Insofar as the undercut is formed by the radial projection, which forms a coupling side stop for the sealing member in the first position, a separate undercut may be omitted, since the sealing member is in the second position in the connected state and thus clears the undercut for engagement of the housing projection.

The invention is also directed to a coupling system having two coupling members according to the foregoing descriptions, wherein the respective sealing member of the coupling members is movable from the first position to the second position by the respective other coupling member for fluidly connecting the first fluid channels to each other.

Accordingly, the coupling members of the coupling system are complementary in that they comprise at least one structure, such as the closed coupling surface, through which the respective sealing member of the coupling members is movable from the first position to the second position by the respective other coupling member for fluidly connecting the first fluid channels to each other. The fluid communication of the first fluid channels with each other is performed by directly connecting the respective fluid channel openings, by connecting a fluid channel opening of one coupling member with the elastomer member opening of the other coupling member, or by connecting the respective elastomer member openings of the coupling members. In other words, the respective openings surrounded or formed by the respective elastomer member, are brought into overlap at least in sections in a connected state. During a disconnection, any fluid that may still be present in such an opening area is wiped off at the elastomer member surfaces.

In an embodiment, the sealing member is retained in the second position by engagement of the projecting housing projection of at least one of the coupling members with the projecting undercut.

Accordingly, the housing projection and the undercut are configured such that the housing portion of the respective other coupling member to be inserted into the coupling side opening of one coupling member forms a stop for the sealing member of the one coupling member in the second position when the housing projection engages the undercut.

In conjunction with a spring member and/or with at least a partially elastic design of the sealing member, the sealing member may also secure the engagement of the housing projection in the undercut.

Further advantages of the coupling system additionally result analogously to the advantages listed for the coupling member.

BRIEF DESCRIPTION OF THE DRAWING FIGURES

Features, expediencies and advantages of the invention are also described below by means of embodiments with reference to the drawings.

DETAILED DESCRIPTION

Figure 1:
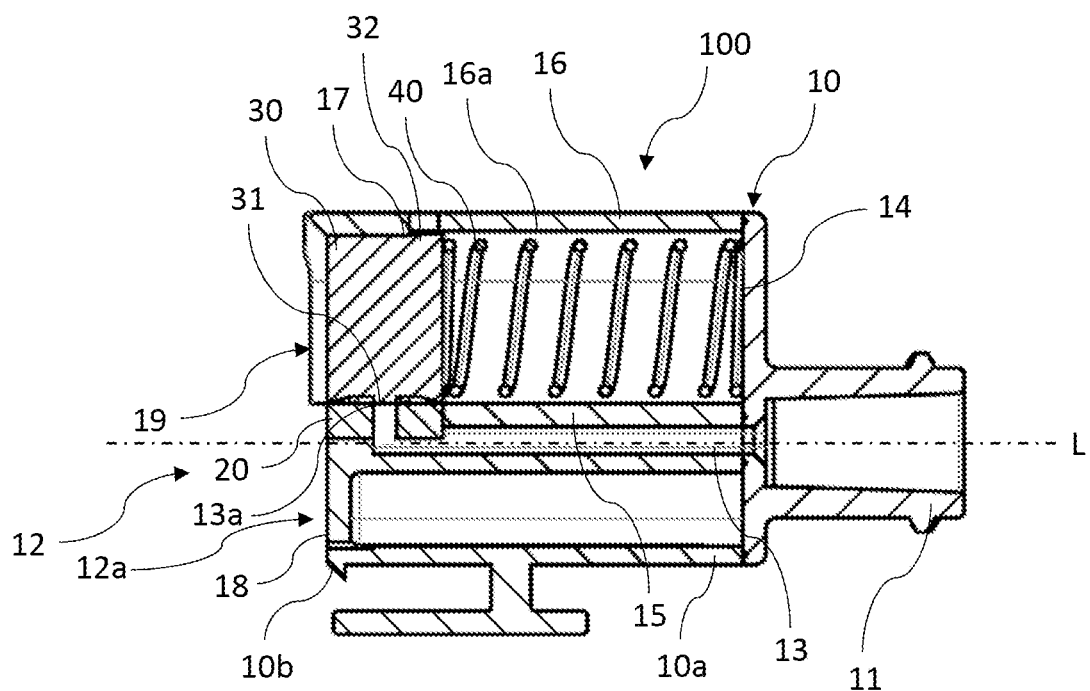
FIG. 1 is a schematic cross-sectional view of a coupling member in a plane parallel to the longitudinal axis of the coupling member housing according to an exemplary first embodiment of the coupling member in the disconnected state.

FIG. 1 shows a cross-sectional view of a coupling member 100 in a plane parallel to the longitudinal axis L of the coupling member housing 10 of the coupling member 100 in a first embodiment. The intersection line corresponds to the intersection line A-A of the coupling system 1000 with coupling members 100' of the second embodiment shown in FIG. 5. The longitudinal axis L of the coupling member housing 10 extends from a fluid connection 11 toward a coupling side 12 having a coupling side front surface 12a. Starting from the fluid connection 11, a first fluid channel 13 initially extends parallel to the longitudinal axis L of the coupling member housing in the direction of the coupling side 12. The first fluid channel 13 comprises a fluid channel opening 13a facing the coupling side, which is formed parallel to the longitudinal axis L of the coupling member housing 100. To this end, a portion of the first fluid channel 13 on the coupling side extends perpendicularly to the course of the first fluid channel parallel to the longitudinal axis L. The perpendicular extending portion with the fluid channel opening 13a is surrounded by an elastomer member 20. For this purpose, the elastomer member 20 is arranged in the direction of the longitudinal axis between an inner wall 15 and the coupling side front surface, wherein a surface of the elastomer member 20 in the direction of the longitudinal axis L on the side of the fluid channel opening 13a is substantially flush with the fluid channel opening 13a. The term "substantially" is directed to the fact that the elastomer member 20 is preferably formed in such a way that it projects in its elastic expansion region in a uncompressed state beyond the fluid channel opening 13a in order to generate a surface pressure in interaction with a counter surface, such as the sealing surface 31 of the sealing member 30, as will be described below, or an elastomer member 20 of a corresponding coupling member 100 or 100' to be connected.

In a disconnected state, as shown in FIG. 1, the fluid channel opening 13a is sealed by the sealing member surface 31 of the sealing member 30 so that no fluid may leak out of the coupling member housing through the fluid channel opening 13a. In this disconnected state, the sealing member surface 31 is in a first position. To expose the fluid channel opening 13a, the sealing surface 31 may be moved from the first position in the direction of the longitudinal axis L to a second position at a smaller distance from the fluid connection 11. In the embodiment shown, the movement of the sealing surface 31 takes place via the guided movement of the sealing member 30 between an outer wall 16, which here corresponds to the outer wall 10a of the coupling member housing 10, and an inner wall 15, which surrounds the first fluid channel 13. Accordingly, the coupling member 100 may also be divided into a fluid channel side portion and a sealing member portion, wherein the portions extend side by side in the direction of the longitudinal axis L. Here, the movement of the sealing member 30 and thus the sealing surface 30 is carried out from the first to the second position against a spring force of a spring member arranged between the sealing member 30 and a fluid connection side portion 14. Consequently, the fluid channel opening 31a is only exposed by selective application of force, which reduces the risk of unintentional fluid leakage. In addition, a restoring force is applied by the spring member so that the fluid channel opening 13a is automatically resealed upon disconnection.

The outer wall 16 of the coupling member housing 10 also forms, on the coupling side 12, a radially inward projecting projection 17 with respect to the longitudinal axis L. In the first position, this projection interacts with a sealing member projection 32 which projects radially outwards with respect to the longitudinal axis L and is arranged on a side of the sealing member 30 facing the fluid connection 11. Thus, the sealing member 30 is retained in the first position in conjunction with the spring member 40. However, in the embodiment shown, the radial projection 17 also serves to receive a housing projection 10b of a corresponding coupling member 100 or 100' to be connected, which will be described later.

The coupling member housing 10 also forms, together with the elastomer member 20, a closed coupling surface 18 on the coupling side front surface 12a, which encloses a coupling side opening 19. The term coupling side opening does not refer to a lateral opening, but to an opening on the coupling side, more specifically to an opening on the coupling side front surface 12a. In a disconnected state, the coupling side opening 19 is filled by the sealing member 30 so that the coupling side front surface 12a is formed substantially flat. The term "substantially" is directed to the fact that the coupling side front surface 12a may still comprise minor protrusions, such as centering aids formed over the coupling member housing 10 for connection. However, such protrusions do not noticeably impede accessibility of the coupling side front surface, so that disinfectability is facilitated.

The housing projection 10b already indicated projects radially outwardly with respect to the longitudinal axis from an external wall 10a of the coupling member housing 10, which extends in the direction of the longitudinal axis L. In the embodiment shown, the housing projection 10b is provided in a region of the external wall 10a that is located outside the coupling side opening 19, more specifically, radially opposing the radial projection 17 with respect to the longitudinal axis L in this case. In particular, the housing projection 10b is formed by a coupling side end portion of the external wall 10a of the coupling member housing 10. In this case, the housing projection 10b forms a snap hook that is radially movable with respect to the longitudinal axis L in order to interact with a projection of a corresponding coupling member 100 or 100' to be connected, such as the projection 17, that faces radially inward with respect to the longitudinal axis. In this embodiment, the housing projection 10b is attributed to the closed coupling surface 18, even if a movement gap is to be provided between the housing projection 10b and the rest of the closed coupling surface 18 for implementing the snap hook movement. Engagement of the housing projection 10b with a corresponding radially inward projection or recess of a coupling member 100 or 100' to be connected may be released by the unlocking mechanism 10c. In the illustrated embodiment, the housing projection 10b is moved radially inwardly and thus out of engagement, for example, by applying a force to the unlocking mechanism 10c with at least one force component that is radial with respect to the longitudinal axis.

Figure 2:
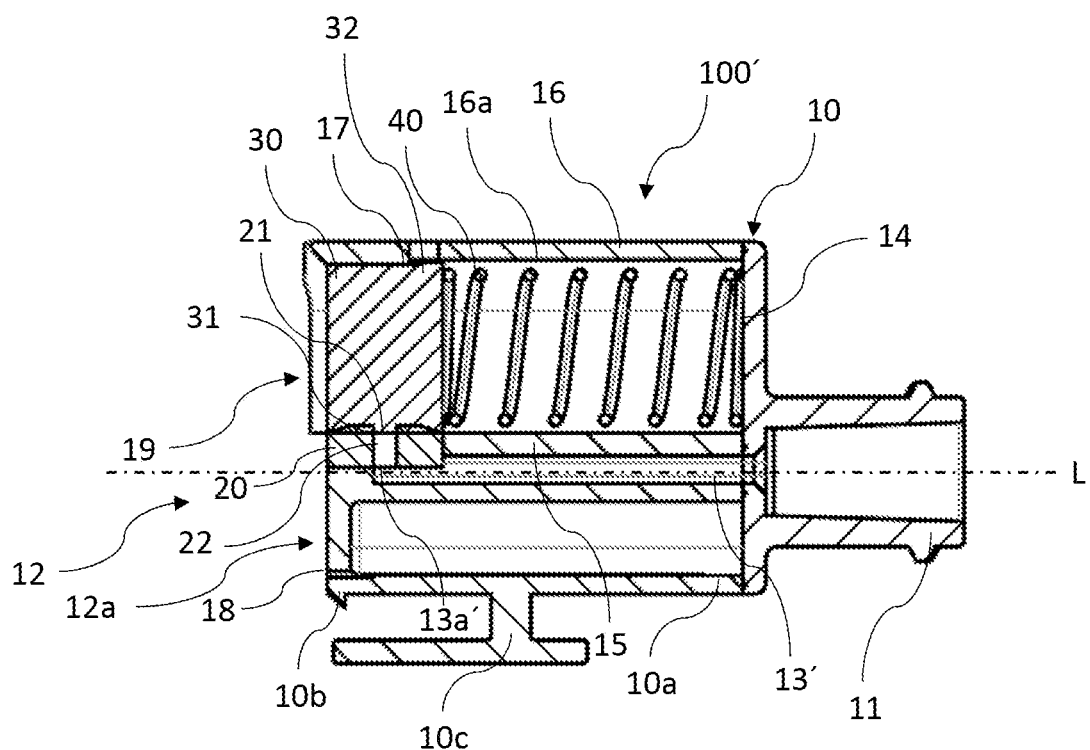
FIG. 2 is a schematic cross-sectional view of a coupling member in a plane parallel to the longitudinal axis of the coupling member according to an exemplary second embodiment of the coupling member in the disconnected state.

FIG. 2 shows a schematic cross-sectional view of a coupling member 100' in a plane parallel to the longitudinal axis L of the coupling member housing 10, according to an exemplary second embodiment of the coupling member 100' in the disconnected state. The second embodiment differs from the first embodiment in that the first fluid channel 13' with the fluid channel opening 13a' is not directly sealed by the sealing surface 31 of the sealing member 30, but the sealing surface 31 of the sealing member 30 seals an elastomer member opening 21 of the elastomer member 20 facing the coupling side 12, which forms a second fluid channel 22 adjoining the first fluid channel 13a'. In other words, the fluid channel for fluid communication with a fluid channel of a corresponding coupling member 100 or 100' to be connected is no longer formed directly by a first fluid channel 13, but by a first fluid channel 13' and a second fluid channel 22. Accordingly, in FIG. 2 the same reference signs are used for identical components, while only other reference signs are indicated for modified components. The contents of the description for the first embodiment are applicable in an analogous manner to the second embodiment, provided that no changes result from the above configuration of the fluid channel.

The formation of a second fluid channel 22 for the continuation of the first fluid channel 13a' enables, for example, a simple adaptation of the design of the elastomer member opening 21 or also a bridging of distances to be provided differently in the radial direction with respect to the longitudinal axis L by replacing the elastomer member 20.

Figure 3:
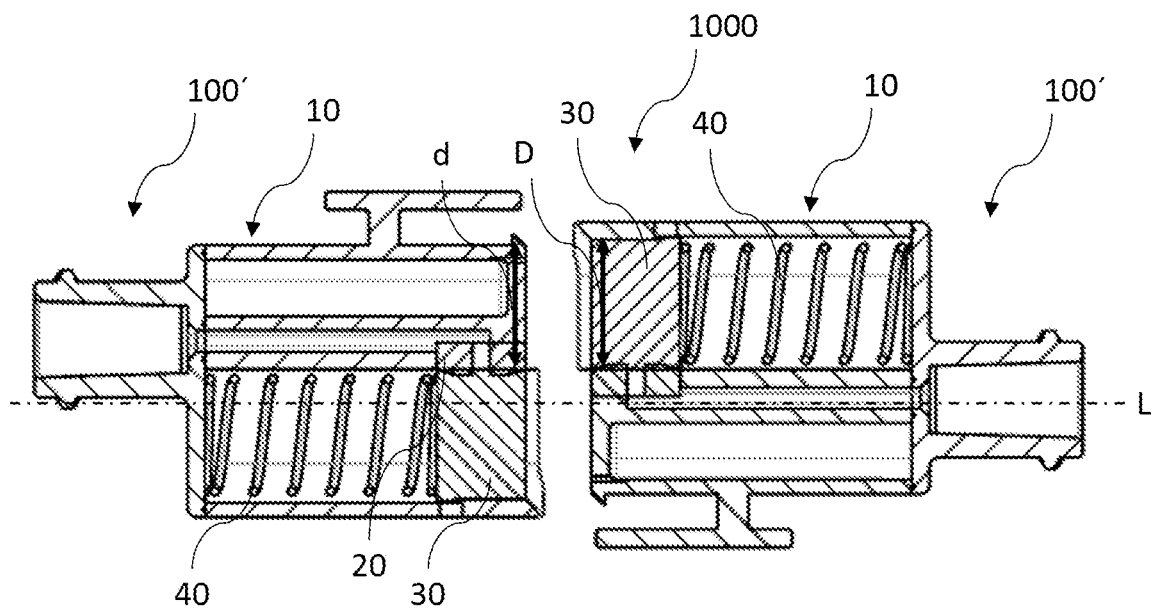
FIG. 3 is a schematic cross-sectional view of a coupling system with two coupling members according to the second embodiment in a plane parallel to the longitudinal axis of the coupling members in the disconnected state.

FIG. 3 shows a schematic cross-sectional view of a coupling system 1000 with two coupling members 100' according to the second embodiment in a plane parallel to the longitudinal axis L of the coupling members 100' in the disconnected state. The detailed structure of the respective coupling members can be derived from FIG. 2 and the associated description. For reasons of simplicity, only the reference signs for the main components are entered in FIG. 3. The coupling members 100' are shown opposing each other. The representation corresponds to an arrangement of the coupling members 100' in which they may be connected to each other by a movement along the longitudinal axis L. According to the illustration, the coupling members, which are identical in design here, are arranged rotated by 180° about the longitudinal axis L, i.e. minor-inverted with respect to the longitudinal axis L. Accordingly, the closed coupling surface 18 of the respective coupling members 100' is opposite the sealing member 30 or the coupling side opening 19 of the respective other coupling member 100'. In this still disconnected state, the respective elastomer member opening 21 of the elastomer member 20 is sealed by the respective sealing surface 31 of the respective sealing member 30.

In addition, FIG. 3 also illustrates once again the ratios of the rigid surface D of the coupling side opening 19 to the rigid surface d of the closed coupling surface 18. Accordingly, for the use of equivalent coupling members 100', the rigid surface D of the coupling side opening 19 is larger than the rigid surface d of the closed coupling surface 18 in order to be able to accommodate the closed coupling surface of a respective coupling member 100' to be connected. In order to be able to ensure sufficient surface pressure between the elastomer members 20 facing each other in the connected state, the rigid surface D should only be larger by an amount that can be compensated by the expansion of the elastomer members 20. The term rigid area may take into account elastically deformable components. Accordingly, the rigid surface d of the closed coupling surface 18 is somewhat smaller than the surface of the closed coupling surface up to the radial end of the housing projection 10b, since it is elastically movable inwardly. In other words, the rigid surface d in this case corresponds to the closed coupling surface 18 minus the radial gap that can be bridged by the housing projection 10b.

Figure 4:
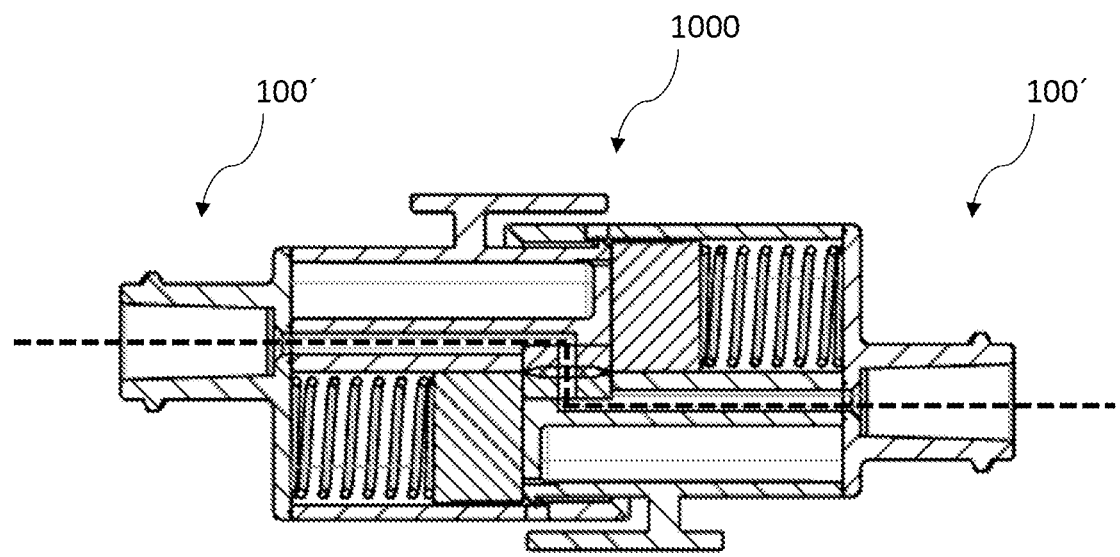
FIG. 4 is a schematic cross-sectional view of the coupling system with the two coupling members according to the second embodiment in a plane parallel to the longitudinal axis of the coupling members in the connected state.
Figure 5A:
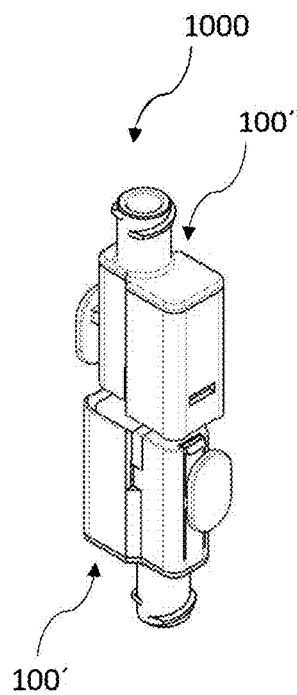
FIG. 5A is an isometric view of the coupling system according to FIGS. 3 and 4 in the disconnected state.
Figure 5B:
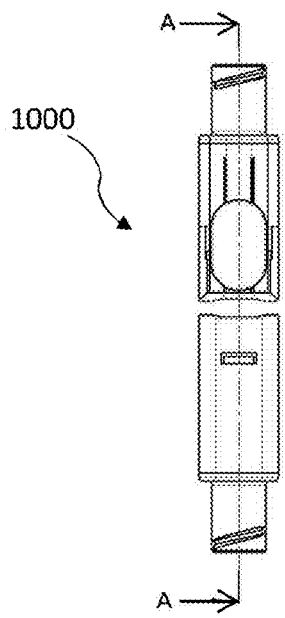
FIG. 5B is a left elevation view of the coupling system according to FIGS. 3 and 4 in the disconnected state.
Figure 5C:
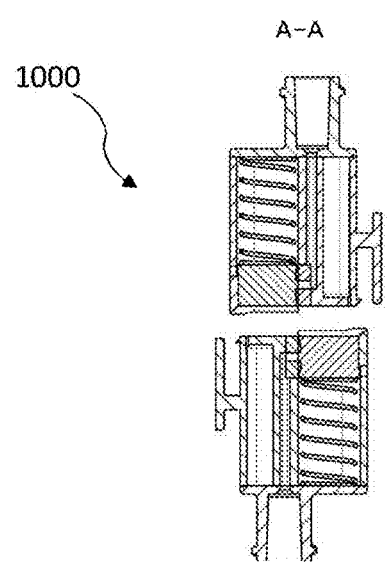
FIG. 5C is a front cross-sectional view of the coupling system according to FIGS. 3 and 4 in the disconnected state, shown in a plane indicated by intersection line A-A in FIG. 5B.
Figure 5D:
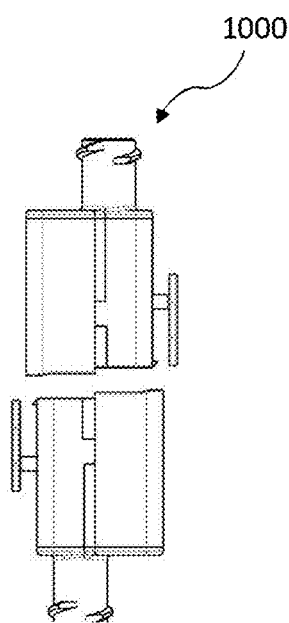
FIG. 5D is a front elevation view of the coupling system according to FIGS. 3 and 4 in the disconnected state.
Figure 5E:
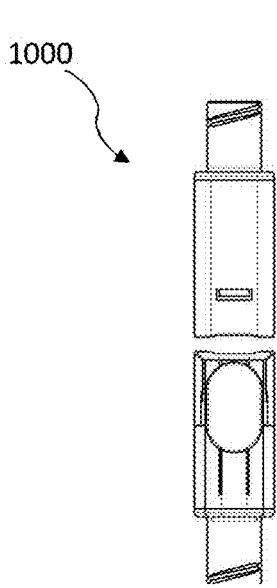
FIG. 5E is a right elevation view of the coupling system according to FIGS. 3 and 4 in the disconnected state.
Figure 5F:
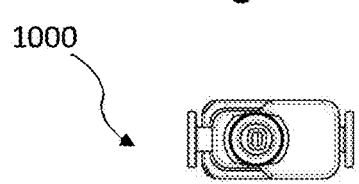
FIG. 5F is a top plan view of the coupling system according to FIGS. 3 and 4.
Figure 5G:
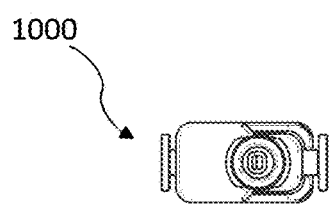
FIG. 5G is a bottom plan view of the coupling system according to FIGS. 3 and 4.

FIG. 4 shows a schematic cross-sectional view of the coupling system 1000 with the two coupling members 100' according to the second embodiment in a plane parallel to the longitudinal axis L of the coupling members 100' in the connected state. Here, also for reasons of simplicity, the reference signs to already described components of the coupling members 100' have been omitted. To achieve the illustrated connected state, for example, one of the coupling members 100' is moved towards the other coupling member 100' to be connected in the direction of the longitudinal axis L. The closed coupling surfaces 19 of the coupling members 100' thereby penetrate into the respective coupling side opening 19 formed by the other coupling member 100' and push the sealing member 30 and thus the sealing surface 31 from the first position, in which the sealing surface 31 seals the elastomer member opening 21, into the second position, in which the sealing surface 31 exposes the elastomer member opening 21. During this movement, the respective elastomer members 20 or the facing surfaces of the elastomer members 20 are simultaneously shifted over each other parallel to longitudinal axis L until the elastomer member openings 21 of the elastomer members 20 overlap. In this position, which corresponds to a second position of the sealing member surface 31, the coupling members 100' are in fluid communication via the respective elastomer member openings 21, the respective second fluid channels 22 and the respective first fluid channel 13a', as illustrated by the dashed fluid flow in FIG. 4. This connected state is maintained by the respective engagement of the housing projection 10b of the respective coupling members 100' with the radial projection 17 of the respective other coupling member 100'. The engagement is further secured by the spring force of the respective spring member 40.

For disconnection from the connected state, the respective housing projection 10b is moved inward in the radial direction with respect to the longitudinal axis L and thus out of the respective radial projection 17 by pushing the respective release mechanism 10c. The spring force of the respective spring member 40 forces the coupling members 100' apart, wherein at the same time the respective sealing surfaces 31 of the sealing members 30 shift over the respective elastomer member openings 21 and seal them completely again upon reaching the first position. The relative movement of the facing surfaces of the elastomer members 20 parallel to the longitudinal axis L wipes off any fluid residues that may be present on these surfaces.

FIGS. 5A-5G show external views of the coupling system according to FIGS. 3 and 4 as well as the sectional view along the intersection line A-A in the disconnected state. This results in further design features of the described embodiment.

The invention is not limited to the described embodiments. In particular, certain features of one embodiment are in principle also applicable to other embodiments, unless reasonably precluded. Even though the coupling system 1000 has been explained with reference to two coupling members 100', the coupling system may also comprise, for example, two coupling members 100 or one coupling member 100 and one coupling member 100', each of which is of complementary design.

The invention claimed is:

1. A coupling member for a closed fluid transfer system, the coupling member comprising:
   A) a coupling member housing comprising a fluid connection and a coupling side, wherein a longitudinal axis of the coupling member housing extends from the fluid connection to the coupling side;
   B) a first fluid channel extending in parallel to the longitudinal axis of the coupling member housing from the fluid connection toward the coupling side to a fluid channel opening facing perpendicular to the longitudinal axis of the coupling member, for fluidly connecting the fluid connection and the coupling side;
   C) at least one elastomer member, which:
      i) surrounds the fluid channel opening of the first fluid channel; or
      ii) forms a second fluid channel adjoining the fluid channel opening of the first fluid channel, wherein an elastomer member opening of the second fluid channel faces perpendicular to the longitudinal axis of the coupling member housing; and
   D) a sealing member having a sealing surface facing the fluid channel opening of the first fluid channel or the elastomer member opening of the second fluid channel,
   wherein the sealing surface is movable along the longitudinal axis of the coupling member housing between a first position, in which the sealing surface seals the fluid channel opening of the first fluid channel or the elastomer member opening of the second fluid channel, and a second position, in which the sealing surface exposes the fluid channel opening of the first fluid channel or the elastomer member opening of the second fluid channel for fluid communication with the coupling side,
   wherein the coupling member housing comprises on an inner surface of the coupling member housing an undercut, and
   wherein the coupling member housing comprises on the coupling side a radial projection with respect to the longitudinal axis, which forms a coupling side stop for the sealing member in the first position, and wherein the undercut is formed by the radial projection.

2. The coupling member according to claim 1, wherein the at least one elastomer member is formed by at least two separate elastomers.

3. The coupling member according to claim 1, wherein the sealing member is retainable in the first position in a direction of the coupling side via a spring member which is supported on a side of the sealing member facing away from the coupling side on a fluid connection side portion or on a portion of the coupling member housing located between a fluid connection side portion and the sealing member.

4. The coupling member according to claim 3, wherein the spring member is a metal spring or elastomer spring.

5. The coupling member according to claim 1, wherein the sealing member is at least partially elastic and is supported on a side of the sealing member facing away from the coupling side on a fluid connection side portion or on a portion of the coupling member housing located between a fluid connection side portion and the sealing surface.

6. The coupling member according to claim 1, wherein the sealing member is guided between an inner wall of the coupling member housing, which surrounds the first fluid channel in a longitudinal direction or extends longitudinally with respect to the longitudinal axis on one side of the first fluid channel, and an outer wall, which is parallel to the inner wall and distanced thereto in an outward direction.

7. The coupling member according to claim 1, wherein the sealing member is guided between an inner wall of the coupling member housing, which surrounds the first fluid channel in a longitudinal direction or extends longitudinally with respect to the longitudinal axis on one side of the first fluid channel, and an outer wall, which is parallel to the inner wall and distanced thereto in an outward direction, and wherein the radial projection is formed by a coupling side portion of the outer wall extending radially inward.

8. The coupling member according to claim 1, wherein the coupling member comprises on a coupling side front surface, a closed coupling surface and a coupling side opening, wherein the coupling side opening is limited to an area closable by a side of the sealing member facing the coupling side front surface.

9. The coupling member according to claim 8, wherein a rigid surface of the coupling side opening perpendicular to the longitudinal axis is larger than a rigid surface of the closed coupling surface perpendicular to the longitudinal axis.

10. The coupling member according to claim 9, wherein the rigid surface of the coupling side opening perpendicular to the longitudinal axis is larger than the rigid surface of the closed coupling surface perpendicular to the longitudinal axis.

11. The coupling member according to claim 8, wherein the at least one elastomer member defines a portion of the closed coupling surface.

12. The coupling member according to claim 1, wherein an external wall of the coupling member housing extending in a direction of the longitudinal axis comprises a housing projection projecting radially outward with respect to the longitudinal axis.

13. The coupling member according to claim 12, wherein the housing projection is formed as an elastic snap hook.

14. The coupling member according to claim 13, wherein the elastic snap hook is attached to a remainder of the external wall of the coupling member housing with a movement gap configured to allow flexing movement of the elastic snap hook.

15. The coupling member according to claim 12, wherein an area of the external wall located on a side of the first fluid channel facing away the sealing member comprises the housing projection projecting radially outward with respect to the longitudinal axis.

16. The coupling member according to claim 12, wherein the external wall of the coupling member housing further comprises an unlocking mechanism that extends radially from the external wall and along the longitudinal axis towards the housing projection.

17. The coupling member according to claim 1, wherein the sealing member is guided between an inner wall of the coupling member housing, which surrounds the first fluid channel in a longitudinal direction or extends longitudinally with respect to the longitudinal axis on one side of the first fluid channel, and an outer wall, which is parallel to the inner wall and distanced thereto in an outward direction, and wherein the inner surface is the inner surface of the outer wall.

18. A coupling system comprising two coupling members according to claim 1, wherein the respective sealing member of the coupling members is movable from the first position to the second position by the respective other coupling member for fluidly connecting the first fluid channels to each other.

19. The coupling system according to claim 18, wherein an external wall of the coupling member housing of at least one of the coupling members extending in a direction of the longitudinal axis comprises a housing projection projecting radially outward with respect to the longitudinal axis, wherein the coupling member housing of at least the other one of the coupling members comprises on an inner surface of the coupling member housing an undercut, and wherein the sealing member of at least the one of the coupling members is retained in the second position by engagement of the housing projection of at least the other one of the coupling members comprising the undercut.

* * * * *